(12) United States Patent
Dela

(10) Patent No.: US 10,010,397 B2
(45) Date of Patent: Jul. 3, 2018

(54) MEDICAL DEVICE RETRIEVAL APPARATUS

(71) Applicant: COOK MEDICAL TECHNOLOGIES LLC, Bloomington, IN (US)

(72) Inventor: Christian Dela, Valby (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 348 days.

(21) Appl. No.: 14/228,721

(22) Filed: Mar. 28, 2014

(65) Prior Publication Data
US 2014/0296905 A1 Oct. 2, 2014

(30) Foreign Application Priority Data

Mar. 28, 2013 (GB) .................................. 1305768.2
Dec. 12, 2013 (GB) .................................. 1321964.7

(51) Int. Cl.
*A61F 2/01* (2006.01)
*A61B 17/50* (2006.01)
(Continued)

(52) U.S. Cl.
CPC .............. *A61F 2/01* (2013.01); *A61B 17/221* (2013.01); *A61B 17/32056* (2013.01);
(Continued)

(58) Field of Classification Search
CPC ........ A61F 2002/9528; A61F 2002/011; A61F 2/01; A61B 2017/2212; A61B 17/32056; A61B 2017/00358; A61B 17/221
See application file for complete search history.

(56) References Cited

U.S. PATENT DOCUMENTS 5,531,788 A 7/1996 Dibie et al.
5,626,605 A * 5/1997 Irie .......................... A61F 2/01
606/200
(Continued)

FOREIGN PATENT DOCUMENTS

CA 2205433 9/2005
GB 2276325 A 9/1994
(Continued)

OTHER PUBLICATIONS

European Communication for EP 14162080.7 (dated Mar. 11, 2016) (5 Pages).
(Continued)

*Primary Examiner* — Thomas McEvoy
(74) *Attorney, Agent, or Firm* — Brinks Gilson & Lione

(57) ABSTRACT

A medical device retrieval apparatus includes a sheath provided with first and second sheath portions arranged coaxially and movable relative to one another between a snaring position and a closed position. A carrier element is disposed in the sheath and is movable at least relative to the first sheath portion. A snare is attached to the carrier. The snare is locatable within the first sheath portion. The first sheath portion includes a chamber in which a medical device is receivable. In the snaring position the snare is locatable between the first sheath portion and a deployment handle. A method of retrieving a medical device is also provided.

26 Claims, 17 Drawing Sheets

(51) Int. Cl.
  *A61B 17/221* (2006.01)
  *A61B 17/3205* (2006.01)
  *A61B 17/00* (2006.01)
  *A61B 17/12* (2006.01)

(52) U.S. Cl.
  CPC .... *A61B 17/50* (2013.01); *A61B 2017/00358* (2013.01); *A61B 2017/12054* (2013.01); *A61F 2002/011* (2013.01); *A61F 2002/016* (2013.01)

(56) References Cited

U.S. PATENT DOCUMENTS

| | | | |
|---|---|---|---|
| 6,071,279 A * | 6/2000 | Whayne | A61B 18/1492 606/41 |
| 6,290,710 B1 | 9/2001 | Cryer et al. | |
| 2002/0045918 A1 | 4/2002 | Suon et al. | |
| 2002/0082639 A1 * | 6/2002 | Broome | A61B 17/221 606/200 |
| 2005/0055046 A1 | 3/2005 | McGuckin, Jr. et al. | |
| 2005/0288704 A1 | 12/2005 | Cartier et al. | |
| 2006/0265002 A1 * | 11/2006 | Huter | A61F 2/013 606/200 |
| 2007/0191880 A1 | 8/2007 | Cartier et al. | |
| 2007/0198050 A1 | 8/2007 | Ravenscroft et al. | |
| 2007/0244504 A1 * | 10/2007 | Keegan | A61F 2/01 606/200 |
| 2008/0188880 A1 | 8/2008 | Fischer et al. | |
| 2010/0030254 A1 | 2/2010 | Chanduszko et al. | |
| 2010/0228280 A1 | 9/2010 | Groothuis et al. | |
| 2012/0078286 A1 | 3/2012 | Salik | |

FOREIGN PATENT DOCUMENTS

| | | |
|---|---|---|
| WO | WO 2000/16846 A1 | 3/2000 |
| WO | WO 2004/096089 A2 | 11/2004 |
| WO | WO 2010/091212 A1 | 8/2010 |

OTHER PUBLICATIONS

Examination Report for Great Britain Patent Application Serial No. GB1305768.2 dated Apr. 6, 2016, 3 pages.
European Extended Search Report for EP 14162080.7 (dated Jan. 7, 2015) (7 Pages).
Combined Search and Examination Report for Great Britain Patent Application Serial No. 1305768.2 dated Sep. 2, 2013, 6 pages.
Examination Report for Great Britain Patent Application Serial No. 1305768.2 dated Apr. 29, 2015, 3 pages.

* cited by examiner

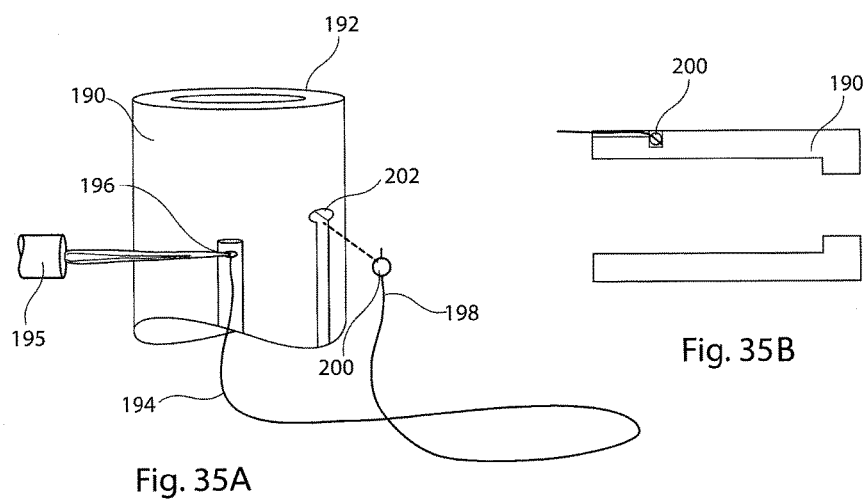
Fig. 35B
Fig. 35A
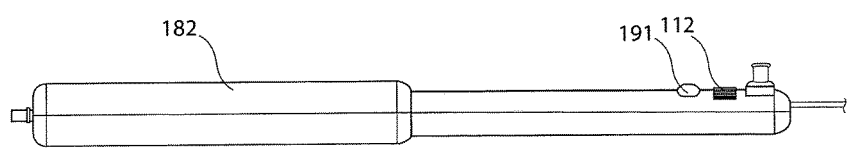
Fig. 35C

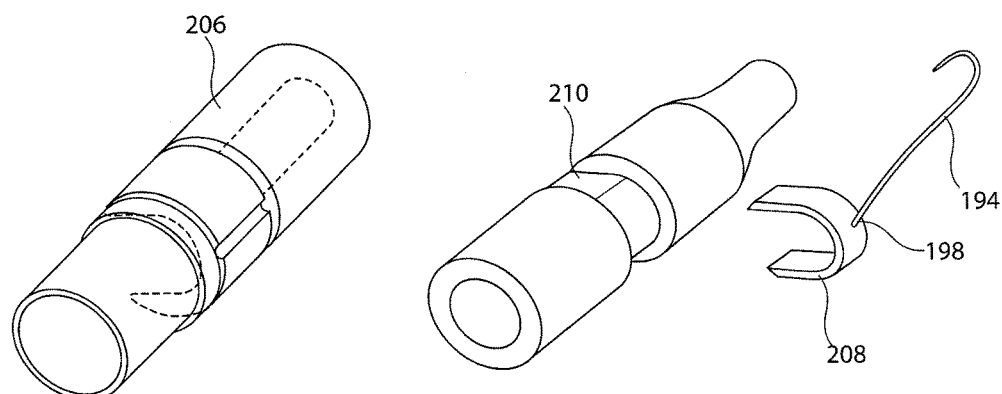
Fig. 37A
Fig. 37B
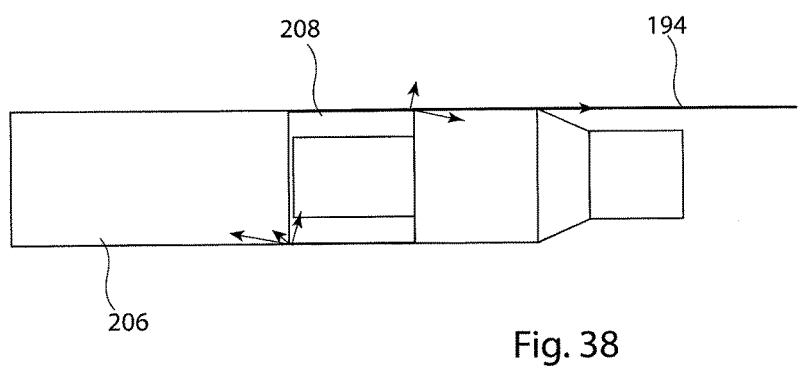
Fig. 38

MEDICAL DEVICE RETRIEVAL APPARATUS

CROSS REFERENCE TO RELATED APPLICATIONS

This application is related to and claims the benefit of priority to British patent application number GB 1305768.2, filed Mar. 28, 2013, and British patent application number GB 1321964.7, filed Dec. 12, 2013, both of which are incorporated herein by reference in their entireties.

TECHNICAL FIELD

The present invention relates to retrieval apparatus for retrieving a medical device from a patient's vessel. The preferred embodiment relates to a device for retrieving a filter in the vena cava.

BACKGROUND

The present invention relates to retrieval apparatus for retrieving a medical device from a patient's vessel. The preferred embodiment relates to a device for retrieving a filter in the vena cava.

Many types of implantable medical devices are intended to be employed in the vasculature of a patient for a limited period only, typically during the course of a medical treatment or while the patient is suffering from an ailment. Devices which are typically retrieved after a period of use include vena cava filters. These are deployed in the patient's vessel, left in position for a period during which filtration is deemed necessary and then removed from the patient. Effective designs of vena cava filters have a tulip or generally conical shape, which have been found to provide good filtration and a natural tendency for the wide end of the filter to open radially outwardly as a result both of the spring force generated by the filter structure and of the pressure from the blood stream. Such filters have proven to be very effective both in terms of filtration and in terms of reliably remaining in position in the vessel.

It is typical to deploy such filters via the femoral or jugular into the vena cava. On the other hand, as a result of their tulip or conical shape and the retrieval geometry, the withdrawal of such filters from the patient's vasculature is normally carried out from the jugular side. Such retrieval can involve the formation of a second percutaneous entry into the patient. It is not generally possible to remove such filters from the femoral side given the fact that the legs of the filter splay outwardly towards the vessel wall and usually have hooks or barbs to hold the filter in position.

There have been attempts to design filter assemblies which allow retraction of the filter from the deployment side. However, these normally involve a modified filter.

Examples of retrievable vascular filter assemblies can be found in US-2002/0045918, US-2005/0055046, US-2010/0030254, U.S. Pat. No. 5,531,788, US-2007/0198050 and US-2012/0078286.

SUMMARY

According to an aspect of the invention, there is provided medical device retrieval apparatus including a sheath provided with first and second sheath portions arranged coaxially and movable relative to one another. A carrier element is disposed in the sheath and movable at least relative to the first sheath portion. A snare may be attached to the carrier, the snare being locatable within the first sheath portion. The first sheath portion can include a chamber in which a medical device is receivable. When in the snaring position the snare can be locatable between the first sheath portion and a deployment handle.

According to another aspect of the present invention, there is provided a method of retrieving a medical device from a patient by means of retrieval apparatus which includes a sheath provided with first and second sheath portions arranged coaxially and movable relative to one another between closed and open sheath positions. A carrier element can be disposed in the sheath and movable at least relative to the first sheath portion. A snare can be attached to the carrier, the snare being locatable within the first sheath portion, the first sheath portion providing a chamber for holding a medical device. In a first step, the method includes locating the sheath across a medical device to be retrieved with the first and second sheath portions extending either side of the medical device. In a second step, the method includes moving the first and second sheath portions away from one another so as to expose the snare. In a third step, the method includes capturing the medical device in the snare. In a fourth step, the method includes pulling the medical device into the chamber of the first sheath portion. In a fifth step, the method includes closing the first and second sheath portions together with the medical device housed in the first sheath portion.

BRIEF DESCRIPTION OF THE DRAWINGS

FIG. 35A is a schematic diagram of an embodiment of a bail-out mechanism for a retrieval apparatus in accordance with one embodiment of the present invention;

FIG. 35B is a schematic diagram in side cross sectional view of the bail-out mechanism of FIG. 35A;

FIG. 35C is a schematic diagram in side view of a handle apparatus including a bail-out mechanism actuator in accordance with the principles of the present invention;

FIG. 37A is a schematic perspective view of a bail-out mechanism in accordance with another embodiment of the present invention;

FIG. 37B is a schematic exploded view of the bail-out mechanism of FIG. 37A; and FIG. 38 is a force diagram of the bail-out mechanism of FIGS. 37A-B.

DETAILED DESCRIPTION

Figure 1:
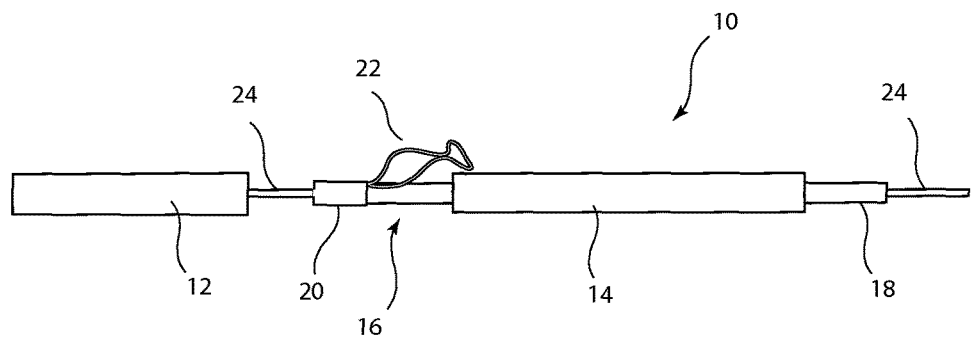
FIG. 1 is a schematic diagram of the sheath components of a preferred embodiment of retrieval apparatus in accordance with one embodiment of the present invention.

The present invention seeks to provide improved medical device retrieval apparatus.

According to an aspect of the present invention, there is provided medical device retrieval apparatus including a sheath provided with first and second sheath portions arranged coaxially and movable relative to one another; a carrier element disposed in the sheath and movable at least relative to the first sheath portion, and a snare attached to the carrier, the snare being locatable within the first sheath portion; the first sheath portion providing a chamber for holding a medical device.

According to an aspect of the invention, there is provided medical device retrieval apparatus including a sheath provided with first and second sheath portions arranged coaxially and movable relative to one another; a carrier element disposed in the sheath and movable at least relative to the first sheath portion, and a snare attached to the carrier, the snare being locatable within the first sheath portion; the first sheath portion including a chamber in which a medical device is receivable.

Advantageously, the first and second sheath portions are configurable to a closed position in which the first and second sheath portions abut one another or in which one of the first and second sheath portions partially overlaps the other.

Thus, the first and second sheath portions are able to be closed and hold therewithin the internal components of the apparatus, in practice to allow movement of the apparatus within the vasculature of the patient in a manner analogous to a conventional one-piece sheath or catheter. The medical device, once retrieved, is housed, preferably entirely, in the first sheath portion for removal from the patient's vasculature.

The snare is in one embodiment a loop of thread or wire. This may be made of metal or metal alloy, such as platinum, palladium, or a shape memory material, for instance a nickel titanium alloy such as Nitinol. It is preferred that the snare is made from or includes radiopaque material.

In some embodiments, the snare includes a thread or wire with a first end attached to the carrier and a second end releasably attached to the carrier. By the term 'thread or wire', it is intended to encompass any suitable filamentary element.

Advantageously, the carrier includes a hub to which the snare is attached.

In a preferred embodiment, the hub is receivable in the first sheath portion, in which case the first sheath portion has an inner diameter which is generally the same as an outer diameter of the hub, the outer diameter of the hub being greater than an outer diameter of the carrier. The hub can thus act as a positioning guide in the first sheath portion.

The sheath in practice has a distal end and a proximal end, the first sheath portion being located at the distal end and the second sheath portion being located at the proximal end. The proximal end is in use the end of the sheath closest to the clinician during the medical procedure and the distal end is the end which is percutaneously inserted into the patient's vasculature. The distal end of the first sheath portion is preferably substantially closed, optionally with the exception of a passage therethrough for an inner catheter and/or a guide wire.

The snare is advantageously located at a proximal end of the hub, that is, an end of the hub facing the proximal end of the sheath.

The assembly advantageously includes a deployment handle coupled to the proximal end of the sheath and in practice to the second sheath portion.

The deployment handle preferably includes an actuator for moving the first and second sheath portions relative to one another. Advantageously, the deployment handle also includes a carrier actuator comprising a rotation element for rotating the carrier relative to the sheath, and in practice for rotating the snare so as to assist in its capturing of a hook or other catch element of the medical device to be retrieved.

According to another aspect of the present invention, there is provided a method of retrieving a medical device from a patient by means of retrieval apparatus which includes a sheath provided with first and second sheath portions arranged coaxially and movable relative to one another between closed and open sheath positions, a carrier element disposed in the sheath and movable at least relative to the first sheath portion, and a snare attached to the carrier, the snare being locatable within the first sheath portion, the first sheath portion providing a chamber for holding a medical device; the method including the steps of:

locating the sheath across a medical device to be retrieved with the first and second sheath portions extending either side of the medical device;

moving the first and second sheath portions away from one another so as to expose the snare;

capturing the medical device in the snare;

pulling the medical device into the chamber of the first sheath portion; and closing the first and second sheath portions together with the medical device housed in the first sheath portion.

In practice, the apparatus can be inserted in to the patient's vasculature endoluminally via the same entry point as that used for deployment of the implantable medical device, for instance through the femoral vein, and thus from the same side as the deployment side. The distal end of the sheath, in particular the first sheath portion, is passed beyond the fitted medical device and then the two sheath portions separated to expose the snare. At this point, the snare is attached to the hook or other catch of the medical device and then the carrier pushed into the first sheath portion. The snaring of the medical device causes this to be pulled into the first sheath portion, with the sheath portion typically assisting in compressing the medical device radially. Once located in the chamber of the first sheath portion, the two sheath portions are closed together again and the sheath, with the medical device housed therein, withdrawn from the patient.

The retrieval device can therefore be used to retrieve conventional conical or tulip shaped filters from the same direction as the deployment direction, without any change required to the design or structure of the filter. The apparatus can also be used to retrieve other types of medical device.

According to an aspect of the invention, there is provided a medical device retrieval apparatus including a carrier and a snare, wherein the snare includes a thread or wire with a first end attached to the carrier and a second end releasably attached to the carrier.

According to another aspect of the invention, there is provided a method of withdrawing a medical device retrieval apparatus from a patient, wherein the medical device retrieval apparatus includes a carrier and a snare, the snare including a thread or wire with a first end attached to the carrier and a second end releasably attached to the carrier, and a snare release actuator for releasing the second end from the carrier; the method including actuating the snare release actuator to release the second end from the carrier; and withdrawing the apparatus from a patient.

A medical device retrieval apparatus can include first and second sheath portions which are coaxial with one another and which are moveable from a closed position in which they abut to an open position in which they are separated from one another. Within the sheath portions there can be provided a snare in the form of a loop of wire, carried on a carrier catheter. The assembly can be pushed past a medical device in a patient's lumen, with the medical device being drawn into the distal sheath section, for subsequent withdrawal from within the patient. The assembly enables retrieval of the medical device from the same direction as the direction in which it was deployed, for example via the femoral vein.

Description of the Preferred Embodiments

Described below are preferred embodiments of the apparatus taught herein. It is to be understood that the drawings are not to scale and are intended to be merely illustrative of the features and elements of the apparatus and its components taught herein.

The preferred embodiments focus upon the retrieval of a vena cava filter but it is to be understood that the apparatus and teachings herein are not limited to any particular filter or type of medical device. The apparatus could be used for the retrieval of any radially compressible implantable medical device.

Referring first to FIG. 1, there is shown in schematic form the distal ends of a medical device retrieval assembly 10 in what could be described as an open or snaring condition. Assembly 10 includes a first or distal sheath portion 12 which extends to the distal extremity of the assembly. A second or proximal sheath portion 14 extends to the proximal end of the assembly 10, although in FIG. 1 only a short length of the second sheath portion 14 is shown. The two sheath portions 12, 14 are preferably made of the same material and have outer diameters which substantially conform with one another such that the sheath portions 12, 14, when in the closed condition, resemble and behave as a conventional single-piece sheath.

Housed within the sheath portions 12, 14 is a retrieval unit 16 which includes an elongate carrier element 18 in the form of a catheter, which extends to the proximal end of the assembly 10, as will become clearly apparent below, and to a cylindrical hub or connector element 20. The hub 20 is integral with the carrier catheter 18 and may conveniently be bonded or welded thereto, although could equally be formed as a single component with the carrier catheter 18. The hub 20 holds a snare 22 which in this embodiment is a loop of wire, preferably a metal or metal alloy of which examples include platinum, palladium, or a shape-memory alloy such as Nitinol. The specific material used of the snare 22 is not relevant as long as it is suitable for its intended purpose.

The carrier catheter 18 is moveable within the first and second sheath portions 12, 14, as described below. The hub 20 preferably has an outer diameter which is about the same as or only slightly smaller than the inner diameter of at least the distal sheath portion 12 and can conveniently also have the same dimensional relationship with the proximal sheath portion 14.

Disposed slidably within the carrier catheter 18 is an inner catheter 24, which extends from the proximal end of assembly 10 to its distal end and in particular is fixed to the distal end 26 of the first sheath portion 12, as will be explained in further detail below.

The inner catheter 24 can conveniently be used as a guide wire catheter, in which case its distal and proximal ends will be open and it will include a lumen extending along the entire of its length to allow the passage of a guide wire therethrough.

The sheath portions 12, 14 and catheters 18, 24 are made from flexible materials to allow the assembly 10 to track through the vasculature of a patient. In a practical embodiment, the sheath portions 12, 14 may have a structure equivalent to that of conventional one-piece sheaths known in the art and may be formed as a multi-layered structure with inner and outer layers of polymeric material having embedded therewithin a strengthening element which may be typically a coil or braid. The catheters 18, 24 may be made of polymeric material and could have structures similar to the sheath portions 12, 14, but equally could be made of metal or metal alloy and sufficiently thin to be bendable and therefore conformable during their passage through the vasculature of a patient. The hub 20 may be made of metal or metal alloy, which is preferred, but may equally be made of a polymeric material.

Figure 2:
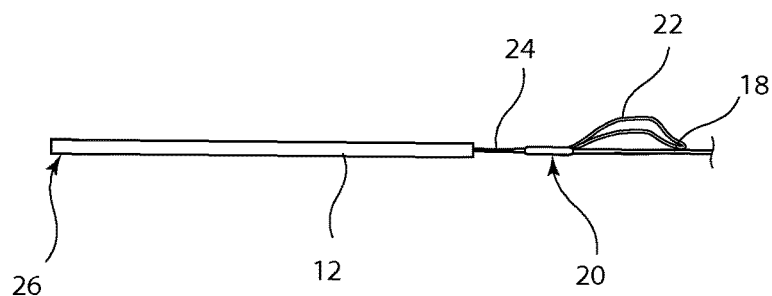
FIGS. 2-3 are detail views of the retrieval apparatus of FIG. 1.

As will be apparent in particular from FIGS. 1 and 2, as well as the subsequent Figures showing the device in operation, the snare 22 is preferably located at the proximal end of the hub 20, that is at the end closest to the sheath portion 14 as viewed from FIG. 1, and extends over the catheter 18. This arrangement can minimize the footprint, that is to reduce the overall diameter of the internal components of the assembly 10, thereby to minimize the outer diameter of the sheath portions 12, 14. In this regard, the outer diameter of the carrier catheter 18 is preferably less than the outer diameter of the hub 20, thereby to accommodate the snare 22 within the space between the carrier catheter 18 and the proximal sheath portion 14.

It is preferred that the snare 22 is made of a springy material, such as one of the materials described above, so that the snare 22 may spring outwardly of the sheath portions 12, 14, as shown in FIG. 1 and subsequent drawings, when released. This assists in the capture of a medical device within a patient's vessel.

Figure 3:
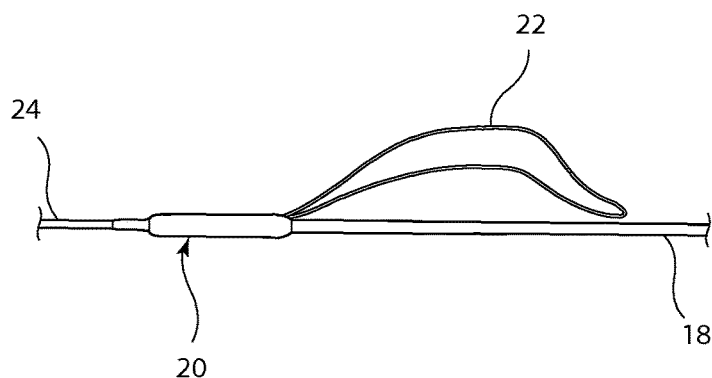

FIGS. 2 and 3 show enlarged views of a portion of the distal end of the assembly 10. In particular, FIG. 2 shows the distal sheath portion 12 with its distal end 26 attached to the inner catheter 24, while FIG. 3 is an enlarged view of one embodiment of hub 20 fixed to the carrier catheter 18.

Figure 4:
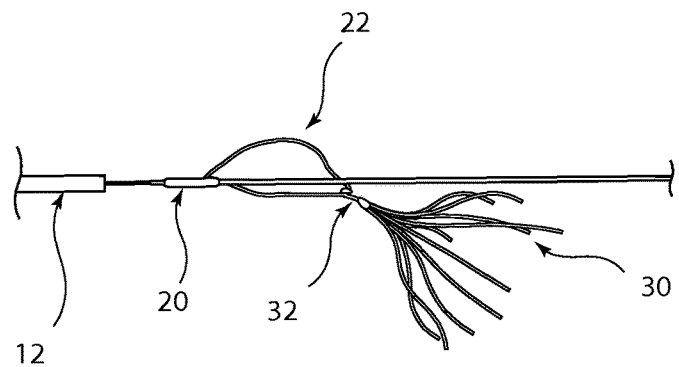
FIGS. 4-8 are detail views of a retrieval apparatus in the process of capturing and retrieving a vena cava filter in accordance with one embodiment of the present invention.
Figure 5:
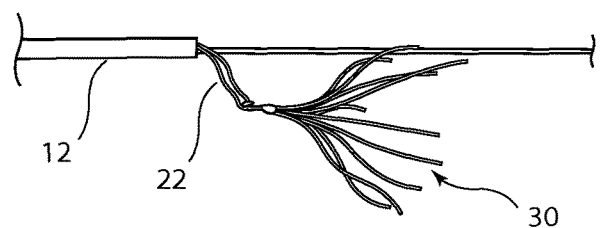
Figure 6:
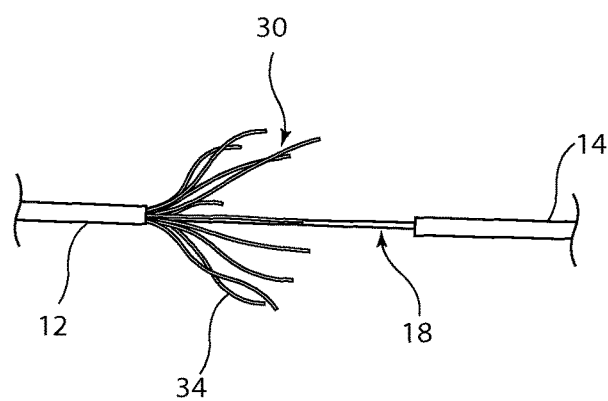

Referring now to FIGS. 4 to 8, these show the sequence of capturing and trapping an implantable medical device, in this case a vena cava filter 30, by means of the apparatus 10. In FIG. 4, a vena cava filter 30 has been captured by the assembly 10, in particular by ensnaring the hook 32 at the narrow end of the filter 30 into the loop of the snare 22. Once captured in the manner shown in FIG. 4, the distal sheath portion 12 is retracted, that is pulled in a proximal direction (equally, the carrier catheter 18 could be pushed in a distal direction so as to push the hub 20 into the chamber formed within the first sheath portion 12). As will be apparent from FIGS. 5, 6 and 7, during the operation of retraction of the first sheath portion 12 (or pushing forwards of the carrier catheter 18) the hub 20 will first enter into the chamber or bore of the first sheath portion 12, pulling with it the snare 22 and filter 30. With the hub 20 having an outer diameter substantially the same as the inner diameter of the distal sheath portion 12, the hub 20 will centre the carrier catheter 18 within the bore of the distal sheath portion 12 and thereby ensure adequate space for receiving the filter 30.

Figure 7:
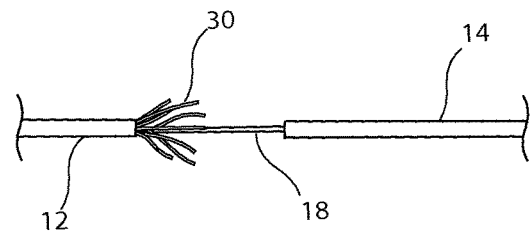

Further retraction of the distal sheath portion 12 (or pushing forwards of the carrier catheter 18) will eventually pull the entirety of the snare 22 into the bore of the inner catheter 12 and with it the hook and closed end of the filter 30. The walls of the lumen of the distal sheath portion 12 act to constrain radially the legs 34 of the filter 30, which will thus collapse towards the carrier catheter 18, allowing the distal sheath portion 12 to be pulled over the filter 30, as is shown in FIG. 7.

Figure 8:
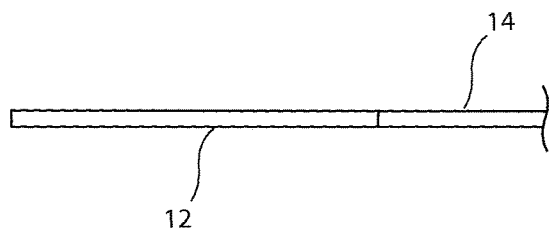

Once the filter 30 has been entirely drawn into the distal sheath portion 12, the sheath is put into the closed position. The proximal sheath portion 14 is brought into abutment with the distal sheath portion 12, as shown in FIG. 8, such that the filter 30 and all the internal components of the assembly 10 are housed within the sheath portions 12, 14. The sheath can then be manipulated as a conventional one-piece sheath.

Figure 9:
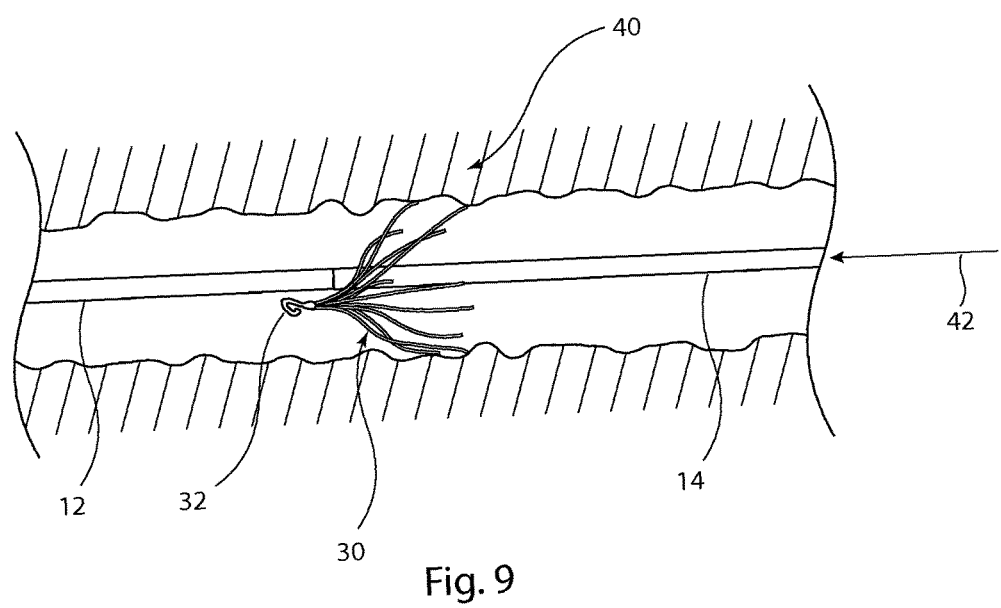
FIG. 9 is a schematic view of the internal components of the distal end of the sheath of FIG. 1 during the capture and retrieval of a filter.
Figure 10:
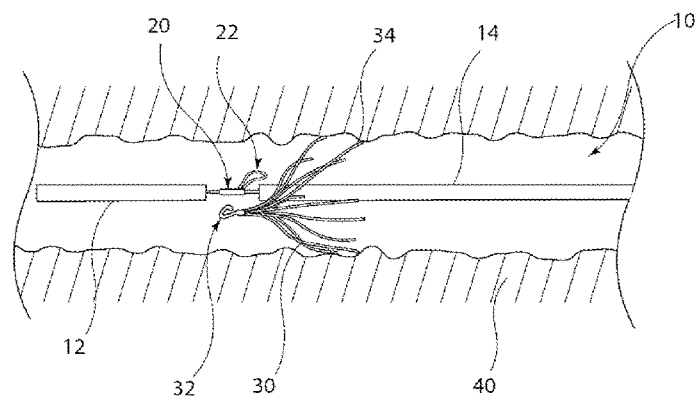
FIGS. 10 and 11A-D are schematic diagrams showing the apparatus in the course of deployment in a vessel adjacent an implanted filter.

Referring now to FIGS. 9 and 10, these are schematic diagrams showing how the apparatus 10 is used to retrieve a medical device disposed within a lumen 40 of a patient. The medical device, in this case a filter 30, is disposed within the patient's vessel 40 with its legs 34 open to the walls of the vessel 40, and these will typically include hooks or barbs to hold the filter 30 in position in the vessel. The hooks or barbs will pierce into the vessel wall.

The closed end of the filter 34, which carries the hook 32, is typically disposed downstream of the vessel, such that the framework created by the legs 34 provides a filter basket for trapping thrombus fragments, plaque and other debris from the bloodstream, in known manner.

The assembly 10 is fed endovascularly in a downstream direction towards the filter 30, that is in the direction of the arrow 42. This is the opposite direction to that conventionally used for the retrieval of such filters. As can be seen, the sheath portions 12, 14, which are closed against one another, can be fed past the filter 30. Subsequently, as shown in FIG. 10, the sheath portions are moved apart from one another to an open or snaring position so as to expose the snare 22 and the internal bore of the distal sheath portion 12, thereby to enable the filter 30 to be captured from its hook and then drawn into the distal sheath portion 12.

Figure 11:
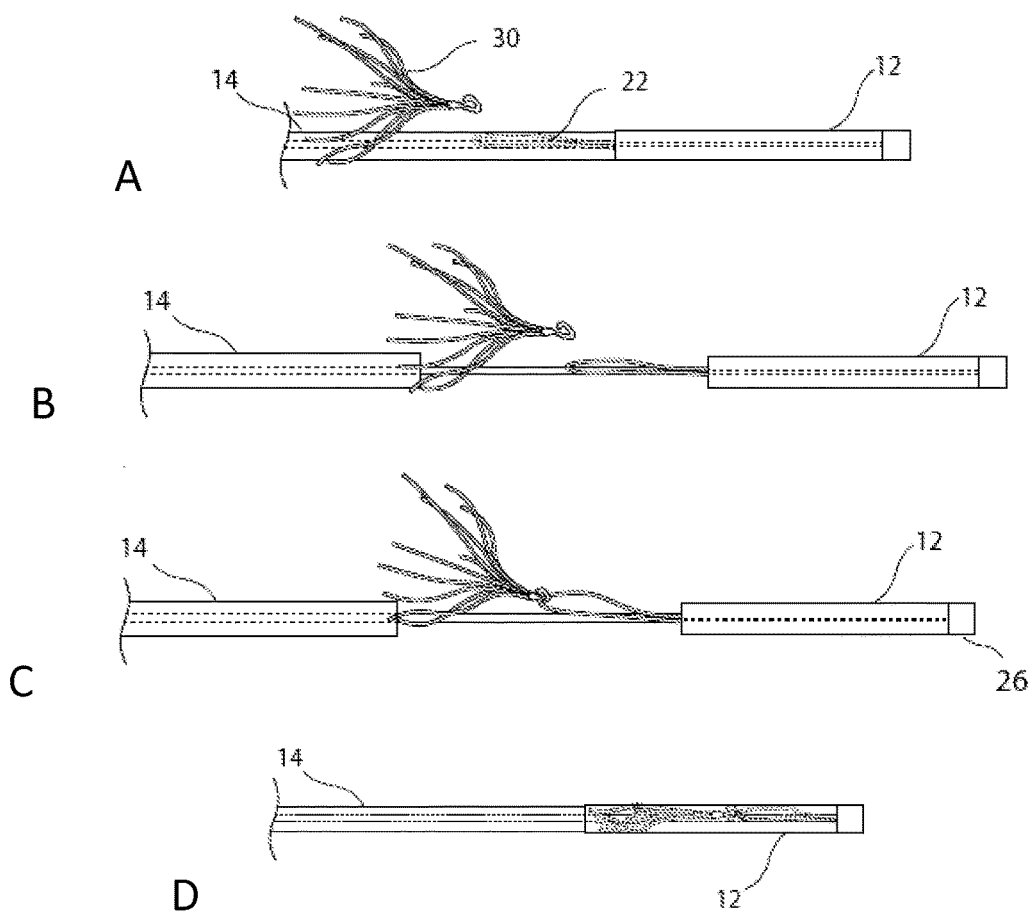

FIGS. 11A-D shows in schematic form the interior of the distal sheath portion 12 in various stages of retrieval of the filter 30. In FIG. 11A, the sheath portions, 12, 14 are in the closed position in abutment against one another, with the snare 22 located within the sheath portion 14. In FIG. 11B, the proximal sheath portion 14 has been pulled back (or the distal portion 12 pushed forwards) so as to create a gap between the two sheath portions 12, 14, thereby exposing the snare 22, which is able to spring outwardly as shown. In FIG. 11C, the hook of the filter 30 has been captured by the snare 22 and is now ready to be pulled into the distal sheath portion 12. In FIG. 11D, the filter has been pulled into the distal sheath portion 12 and the proximal sheath portion 14 has been pushed forwardly (or the distal sheath portion 12 pulled back) so as to cause the two sheath portions 12, 14 to come into abutment again and thereby close the assembly. The filter can then be withdrawn from within the patient's vasculature within the assembly 10, with no risk of any element of the filter 30 snagging against the walls of the patient's vessels during the process.

The sketches of FIGS. 11A-D also show the attachment of the distal end of the inner catheter 24 to the distal end 26 of the distal catheter portion 12, which can usefully be closed, save for the passage of the inner catheter 24 therethrough for a guide wire. The carrier catheter 18 is slidable along the inner catheter 24 and within the sheath portions 12, 14 so it can be pushed into the bore of the distal sheath portion 12.

Figure 12:
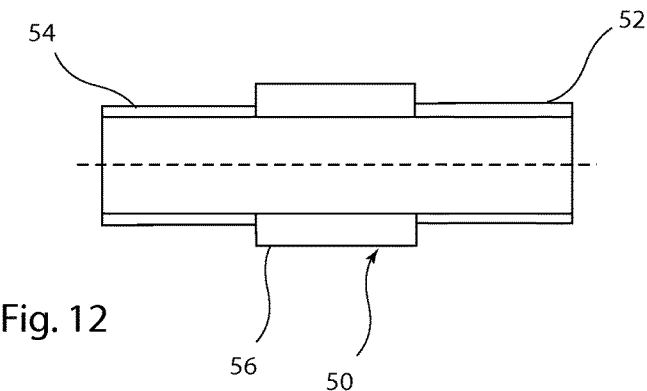
FIG. 12 is a schematic diagram of a connector element for the sheath of a retrieval apparatus in accordance with one embodiment of the present invention.

Referring now to FIG. 12, there is shown an example of connection element which may be used between the distal and proximal sheath portions 12, 14, useful in ensuring that the sheath portions 12, 14 come into aligned abutment with one another. The connector element 50 shown in FIG. 12 includes first and second tubular ends 52, 54, one of which is fixed to one of the sheath portions 12, 14. The other tubular portion 52, 54 is slidably received within the other of the sheath sections 12, 14. This can be achieved by bonding of one of the tubular portions 52, 54 to its respective sheath portion 12, 14 or by having the tubular portions 52, 54 of different diameters, specifically one so as to be a tight friction fit in its respective sheath portion 12, 14 and the other to be a loose fit.

At the center of the connector element 50 there is a provided a body element 56 of wider diameter, against which the ends of the sheath portions 12, 14 abut. It is preferred that when the sheath portions 12, 14 are coupled to the connector 50 that they present a generally smooth outer surface of uniform diameter.

In another embodiment, not shown in the drawings, either the proximal end of the distal sheath portion 12 or the distal end of the proximal sheath portion 14 is flared, that is has a wider inner diameter, such that it can receive the end of the other sheath portion 12, thereby to ensure proper connection between the two sheath portions 12, 14. The skilled person will appreciate that other embodiments designed in accordance with this principle could still have a smooth outer surface, by having stepped walls to the facing ends of the sheath portions 12, 14 so that these can slide over one another.

It will be appreciated that in these examples of connection mechanisms, the two sheath portions 12, 14 will be mechanically coupled to one another so as to ensure that the sheath portions 12, 14 together behave, in terms of pushability, flexibility and therefore trackability, in a manner analogous to a conventional single-piece sheath.

Figure 13:
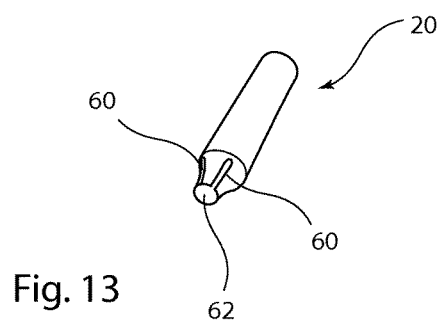
FIGS. 13-15 are detail views of a snare assembly for a retrieval apparatus in accordance with one embodiment of the present invention.
Figure 14:
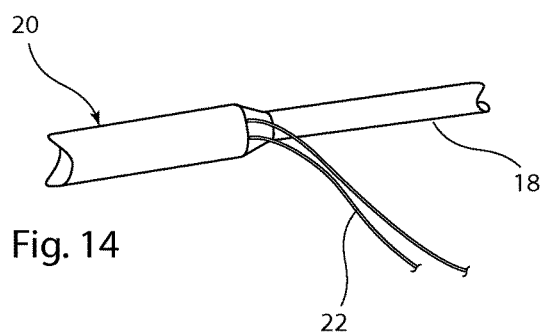
Figure 15:
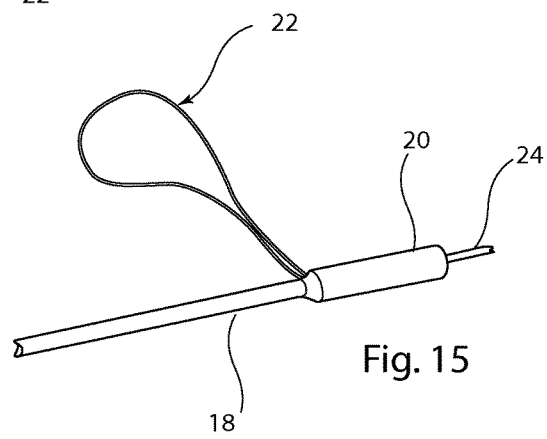

Referring now to FIGS. 13 to 15, there is shown in detail some of the features of a preferred embodiment of hub 20 for the assembly 10 disclosed herein. The hub 20 is formed of a tubular length of material having a tapering proximal end into which two slots 60 are cut. The hub 20 includes an inner bore 62 which receives the distal end of carrier catheter 18 and is typically bonded or welded thereto. This can be seen in particular in FIG. 14. It will be appreciated that when the hub 20 is fitted to the carrier catheter 18, the ends of the slots 60 are in effect closed by virtue of the fact that the extremity of the proximal end of the hub 20 is fixed to the carrier catheter 18. The taper or conical shape of the proximal end of the hub 20 causes the ends of the slots 60 to remain open, thereby to provide the passage for the wire of the snare 22, as can be seen in particular in FIG. 14. Thus, the wire of the snare 22 can be fixed to the hub 20 and in a manner in which the attachment and the snare do not add to the outer diameter of the hub 20, which would otherwise require the provision of a greater inner diameter to the distal sheath portion 12. With this arrangement, the inner diameter of the sheath portion 12 can be practically the same as the outer diameter of the hub 20. The distal end of the hub 20 may also be tapered to assist in its sliding into the bore of the distal sheath portion 12.

Figure 16:
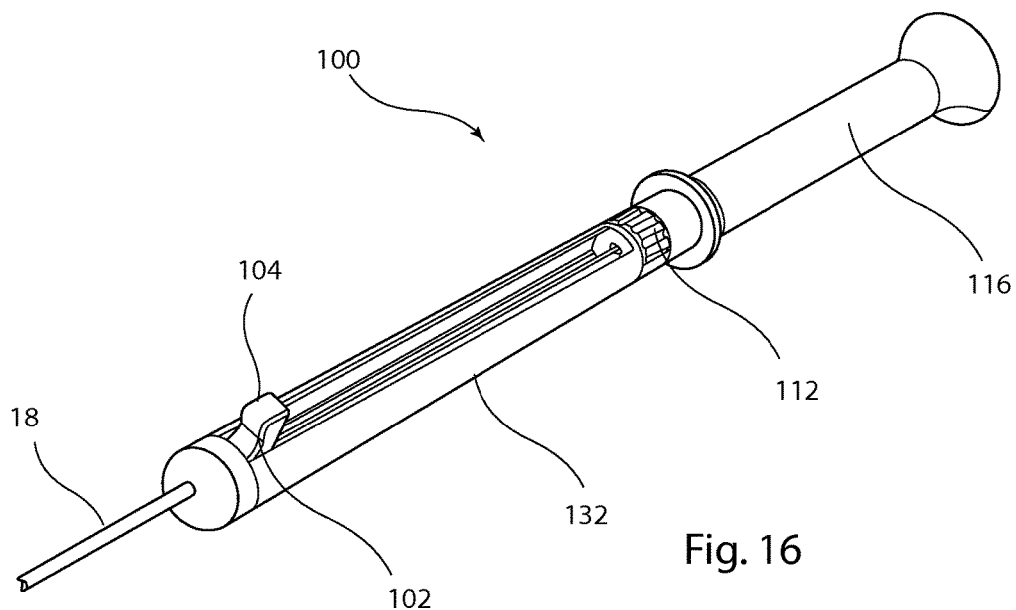
FIG. 16 is a perspective view of an embodiment of a deployment handle for a retrieval assembly in accordance with the principles of the present invention.
Figure 17:
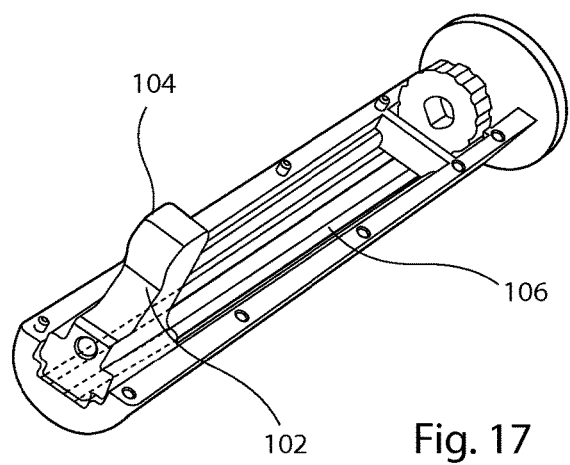
FIGS. 17-23 are perspective views of components of the deployment handle of FIG. 16.

FIGS. 16 to 23 show an embodiment of deployment handle 100 for the assembly 10 disclosed herein. The handle 100 is coupled to the carrier catheter 18 and to the inner catheter 24 and, as will be apparent, provides for activation of the three primary functions of the assembly 10. With reference to FIGS. 16 and 17, the handle includes a first slider 102 which in practice is connected to the proximal sheath portion 14 by any suitable mechanism. The slider 102, which includes a finger-grip 104, is slidable in a proximal direction (rearwardly in the handle 100), typically along guide rails 106. Thus, retraction of the slider 102 will cause retraction of the proximal sheath portion 14 and exposing of the snare 22, as described above. The inner catheter 24 is fixed within the handle assembly 100, so as to maintain the distal end of the assembly 10 in position as the proximal sheath section 14 is pulled back.

Figure 18:
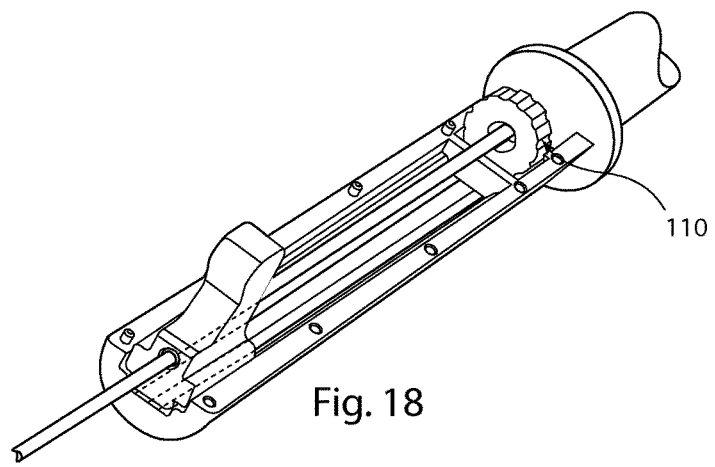
Figure 19:
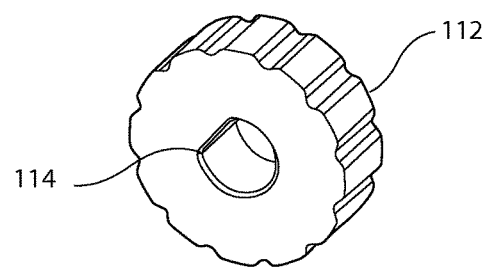

With reference now to FIGS. 18 and 19, these show a rotation mechanism 110 which includes a rotor element 112 which in practice extends out of the housing of the handle 100, as shown in FIG. 16. Rotor 112 includes a part-circular aperture 114 therein which engages with a similar shaped outer wall of the carrier catheter 18, such that rotation of the rotor 112 causes rotation of the carrier catheter 18. In this manner, the distal end of the carrier catheter and in particular the snare 22 carried on the hub 20 can be rotated when in the patient's vessel so as to rotate this into engagement with the hook 32 of the filter 30 or other medical device. Thus, it is not necessary for the clinician to try to rotate or move finely the assembly 100 in an attempt to snare the hook 32 of the filter 30.

Figure 20:
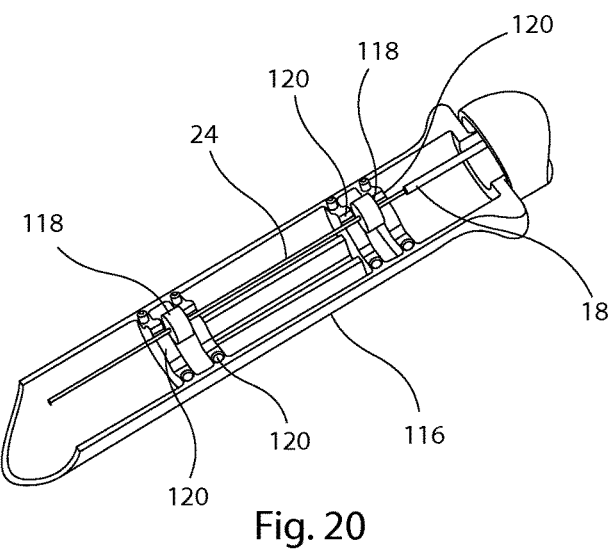

The sheath components 12, 14 of the assembly 10 remain static while the snare 22 is rotated, thus retaining stability of the assembly 10 during this process. For this purpose, as shown in FIG. 20, the inner catheter 24 is held within the handle grip 116 of the handle 100 by first and second gripping elements 118 which keep the inner catheter 24 not only fixed longitudinally in position within the handle 100, but also prevent it from rotating when the carrier catheter 18 is made to rotate. Since the inner catheter 24 does not rotate, neither does the distal sheath portion 12 which is fixed to the inner catheter 24.

Figure 21:
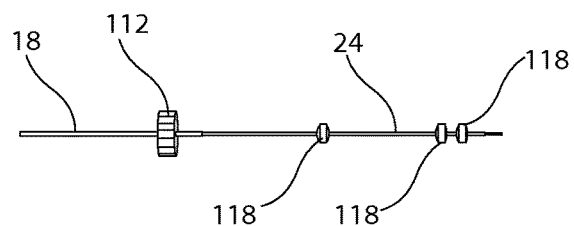

With regard to FIG. 21, which shows three gripper elements 118 fixed to the inner catheter 24, these in this example are metal elements bonded or welded to the inner catheter 24, so as to be integral therewith and reside within appropriate holding walls 120 of the gripper handle 116 in a manner so as not to rotate. As the skilled person will appreciate, this can be achieved by friction fit, by suitable shaping or engaging elements between the grippers 118 and the internal handle walls 120, and so on.

Figure 22:
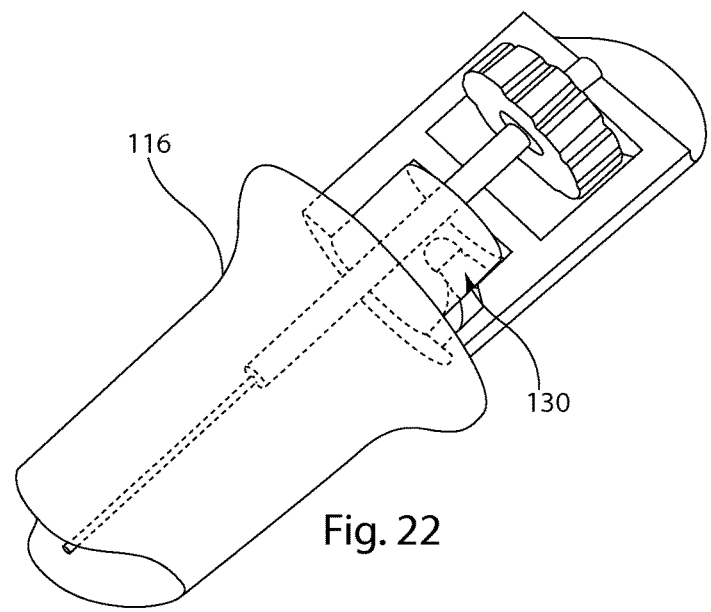
Figure 23:
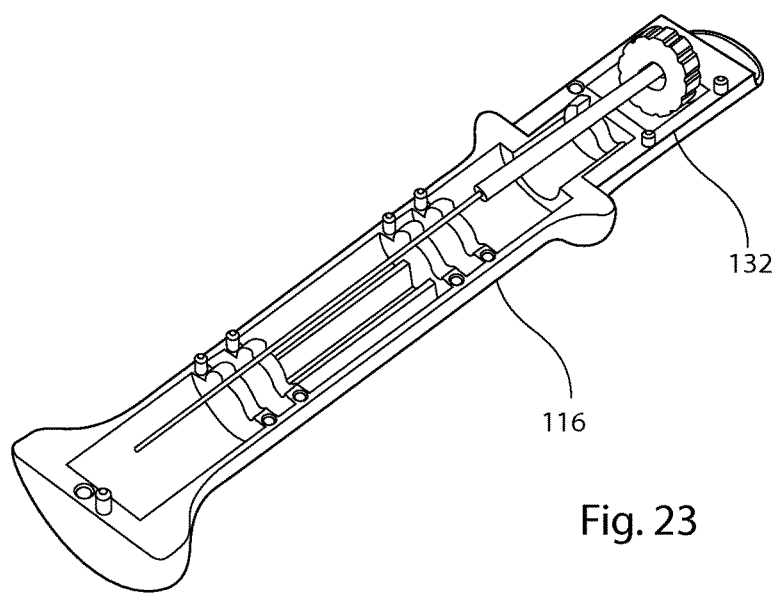

In this embodiment of handle assembly the filter 30, once ensnared by the snare 22, may be drawn into the distal sheath portion 12 by pulling the distal sheath portion 12 backwards (in a proximal direction), rather than by pushing the carrier catheter 18 into the distal sheath portion 12. For this purpose, as shown in FIG. 22, the handle grip 116 includes a bayonet fitting 130 integral with the distal handle section 132, which enables the two handle sections 116, 132 to be decoupled from one another. When so decoupled, the distal handle section 132 is held in position and the proximal or gripper handle section 116 pulled backwards which, by virtue of the inner catheter 24 being fixed to the gripper section 116, will pull the inner catheter and as a result the distal sheath portion 12 backwards, so as to draw the filter 30 into the bore of the distal sheath section 12. Thereafter, the sheath sections 12, 14 can be closed again with relatively little force, by pushing forwards of the slider 102. Once this sequence has been effected and the two sheath sections 12, 14 closed again, the entire assembly 10 can be withdrawn from the patient, with the filter 30 securely held therewithin.

Although not shown in the schematic diagrams, it will be appreciated that the inner catheter 24 will extend through the end wall of the handle assembly 100, so that a guide wire can be passed through the entire assembly 10, 100 for assisting in the deployment and retrieval procedure.

It is not necessary for the inner element 24 to be a catheter, as in some embodiments it could be a rod, for example. Another embodiment, in this regard, provides a rapid exchange facility, in which close to the distal end of the assembly 10 there is provided a side aperture through one of the sheath portions 12, 14 for receiving a guide wire through the side aperture and eventually out through the distal end of the assembly, in a rapid exchange arrangement of the type known in the art.

Figure 24:
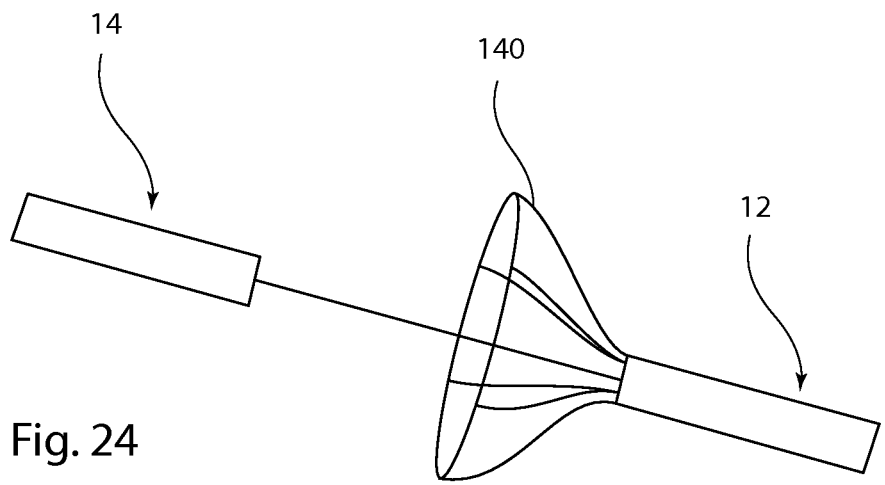
FIG. 24 is a perspective view of a retrieval apparatus having a basket snare in accordance with another embodiment of the present invention.

Referring now to FIG. 24, there is shown in schematic form another embodiment of retrieval apparatus which has the same features as the other embodiments disclosed herein, save for the fact that the snare, instead of being a loop 22 as in the earlier embodiments, is in the form of an expandable basket 140 formed of a series of wires or struts which are able to expand radially outwardly when the sheath sections 12, 14 are separated. The filter 30 can be captured by the snare 140 in a manner similar to that of the loop snare 22, namely by engaging one of the struts of the basket 140 with the hook of the filter 30. Once they are engaged, the basket snare 140 can be pushed into the distal sheath portion 12 in order to draw the filter 30 into the sheath portion 12.

Figure 25:
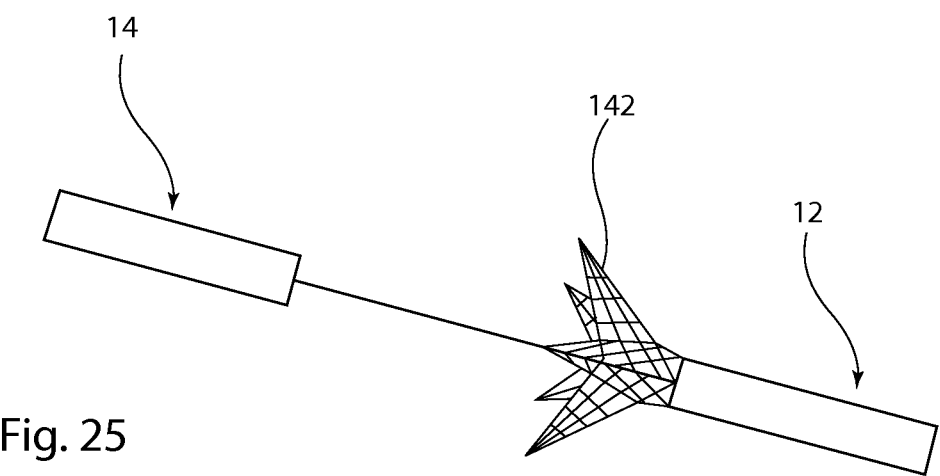
FIG. 25 is a perspective view of a retrieval apparatus having a basket snare in accordance with another embodiment of the present invention.

FIG. 25 shows an embodiment similar to FIG. 24, in which the basket snare 142 is in the form of a mesh of wires in criss-crossing relationship opening out to a series of frame points as shown in FIG. 25. In comparison to FIG. 24, the structure of basket 142 provides a large number of wires and capture points for capturing the hook of a filter 30. The structure, on the other hand, is more voluminous.

An advantage of the designs of snare 140, 142 shown in FIGS. 24 and 25 is that they provide engagement wires or struts circumferentially around the space in the vessel, thereby making it easier to capture a filter 30.

It is to be understood that these snares 140, 142 can be used with all of the features of the apparatus disclosed herein.

Figure 26:
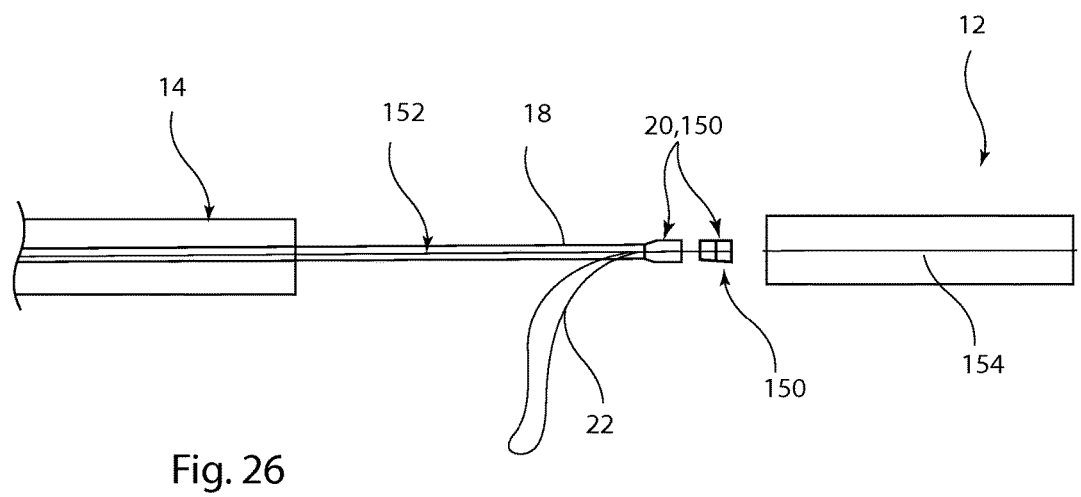
FIG. 26 is a schematic view in partial cross-section of another embodiment of a retrieval apparatus in accordance with the principles of the present invention.

Referring now to FIG. 26, this shows another embodiment of retrieval apparatus which is a slightly modified form of the embodiment described above and in particular as shown in FIGS. 1 to 15. The embodiment of FIG. 26 includes the distal and proximal sheath portions 12, 14, a first rod or preferably cannula 154 which extends the length of the sheath and is fixed to the distal end of the distal sheath portion 12. Carried on the cannula 154 is the cannula 18, to which the snare 22 is attached via the hub 20. In this embodiment, and as possible in all embodiments herein, the cannula 18 may be in the form of a coil of wire of the type typically used in guide wires. Otherwise, it may be a cannula or catheter of solid wall construction.

Located within the cannula 18 is a rod or wire 152 which is fixed to a hub 150, which in turn is coupled to the hub 20 which carries the snare 22. The rod or wire 152 provides additional pushing strength to the assembly in order to push the snare 22 and any filter attached thereto into the distal sheath portion 12.

Figure 27:
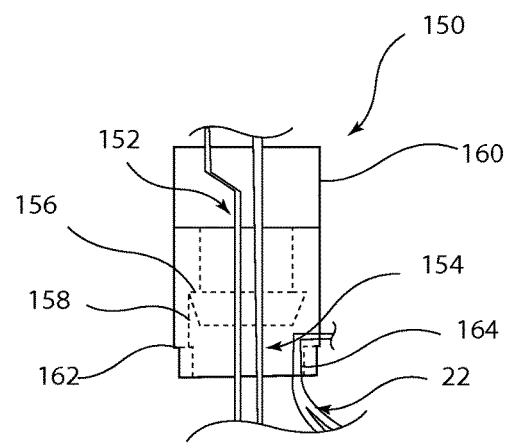
FIG. 27 is an enlarged view of a detail of the hub apparatus of FIG. 26.

FIG. 27 shows an enlarged view of the hub 150 of FIG. 26. As can be seen, the hub 150 includes a first hub component 160 which is coupled to a rotatable second component 162 by a snap fit coupling 156 on the first hub component 160 and corresponding round recess 158 in the second component 162. The two hub components 160 and 162 can thus rotate relative to one another. The ends of the snare 22 are fixed into recesses or bores 164 of the rotatable hub component 162, the snare then passing through the slots 60 of the hub 20, as will be apparent form FIGS. 26 and 15 for example.

The rod or cannula 154 passes through a lumen in the hub components 160, 162, such that the hub 150 can slide along the rod cannula 154. By contrast, the rod or wire 152 attached to the hub 150 is fixed within the first hub component 160 so as to provide control of the hub 150.

Figure 28:
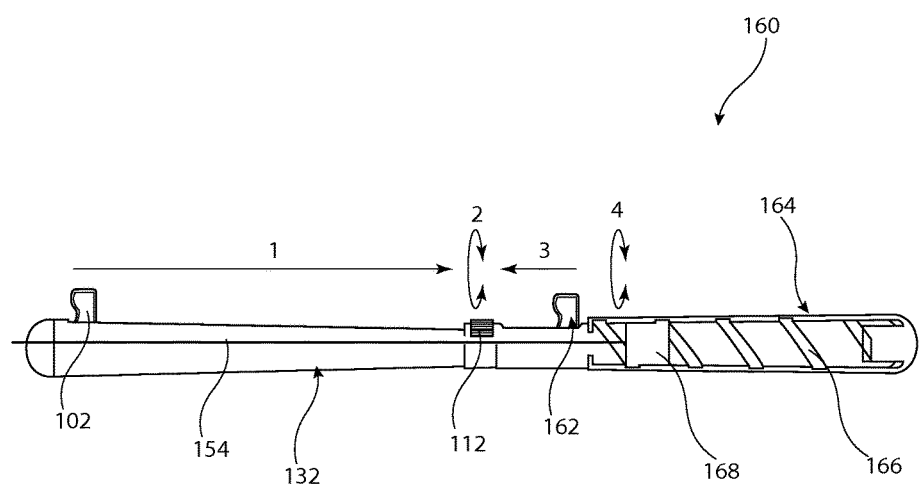
FIG. 28 is a schematic diagram in partial cross-section of another embodiment of a handle for a retrieval apparatus in accordance with the principles of the present invention.

FIG. 28 shows an embodiment of deployment handle useful for operating the embodiment of assembly shown in FIGS. 26 and 27. It is to be understood that the features of FIG. 28 can be used in all of the embodiments described herein. It will be appreciated that the embodiment of the handle 160 of FIG. 28 has characteristics in common with the embodiment of handle shown in FIGS. 16 to 23 and these will be apparent to the skilled person.

The handle 160 includes a first slider 102 which is coupled to the proximal sheath portion 14 and which is slidable in a proximal direction (rearwardly in the handle 160), typically along guiderails similar to those of the embodiment of FIGS. 16 to 23. Retraction of the slider 102 will cause retraction of the proximal sheath portion 14, exposing the snare 22, 140, 142. The handle 160 also includes rotor 112 for rotating the carrier catheter 18 and thus the hub 20 and as a result the snare. In addition, the handle 160 includes a second slider 162 which is coupled to the rod or wire 152 and thus to the hub 150. The slider 162 can be slid forwardly, in practice to push the hub 150, and as a result the hub 20, into the distal sheath portion 12 and in so doing to push the snare 22, 140, 142 and any filter 30 captured thereby into the distal sheath portion 12.

The handle 160 also includes a rotatable grip 164 which includes an internal screw thread 166. Located within the grip 164 is a bushing 168 which is fixed to the wire or cannula 154 and which includes male thread elements which engage with the threads 166 of the grip 164. Rotation of the grip 164 will pull back the threaded bushing 168 and thereby pull back the distal sheath portion 12 towards the proximal sheath portion 14, thereby to close the assembly for removal from the patient, with the filter held securely therein.

The rotatable element 164 of the embodiment of FIG. 28 in effect replaces the pull-back handle portion 116 of the embodiment of the handle 100 shown in FIGS. 16 to 23. The skilled person will appreciate that the handle 100 could be modified to include a rotatable handle element 164 in replacement of the grip 116.

Figure 29:
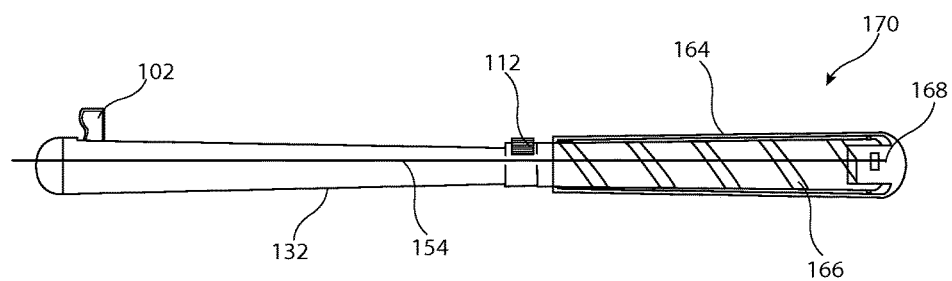
FIG. 29 is a schematic diagram in partial cross section of yet another embodiment of a handle for a retrieval apparatus in accordance with the principles of the present invention.
Figure 30:
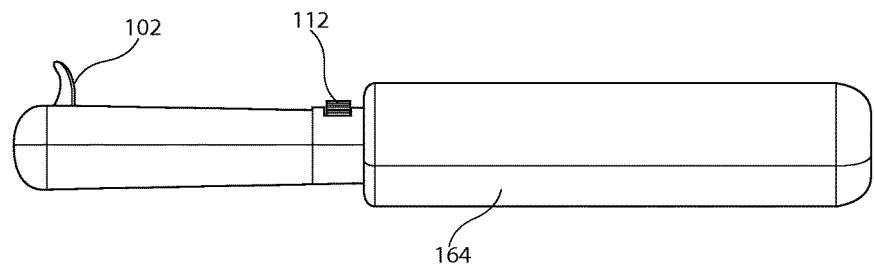
FIG. 30 is a side view of a handle for a retrieval apparatus in accordance with one embodiment of the present invention.
Figure 31:
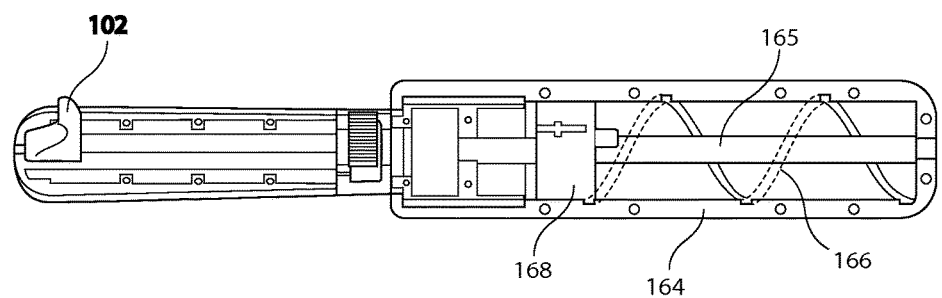
FIG. 31 is a partial cross-sectional view of a handle for the retrieval apparatus of FIGS. 28 and 29.

FIGS. 29-31 show an embodiment of a deployment handle 170 similar in many respects to the deployment handle of FIG. 28. However, in the deployment handle 170, the second slider 162 is not included, nor is the wire 152 to which it is coupled.

The grip 164 includes a bushing guide 165, shown in FIG. 31. The bushing guide 165 can also be included in the embodiment of FIG. 28. The bushing guide 165 extends longitudinally along the grip 164 at least for the distance along which the bushing 168 can travel, preferably centrally in the grip 164, so that the bushing is always located on the bushing guide. The bushing guide 165 is in the embodiment of FIGS. 29-31 a rod with a rectangular cross-section. However, other non-circular cross-sections can be used in other embodiments as long as they ensure that the bushing 168 cannot rotate with respect to the bushing guide 165.

The bushing guide 165 ensures that the bushing 168 does not rotate together with the grip 164 when the grip 164 is rotated. It is particularly advantageous when the lumen of the cannula 154 is located off-center with respect to the deployment handle 170. The cannula 154 is preferably attached to the bushing 168 off-center, and when retracted, it should not rotate around the bushing guide 165. The non-circular cross-section of the bushing guide 165 can ensure this is the case.

In order to move the sheath to an open position, the slider 102 is moved proximally to retract the proximal sheath portion and thereby expose the snare.

Once the filter has been captured by the snare, instead of advancing the hub into the distal sheath portion, the grip 164 is rotated in order to retract the threaded bushing 168 and thereby move the distal sheath portion towards the proximal sheath portion so as to draw the filter into the bore of the distal sheath portion and to move the sheath portions together again to close the sheath. In FIG. 29, the threaded bushing 168 is shown in the fully retracted position.

In a modification, rotation of the grip can draw the filter into the bore of the distal sheath portion, but the sheath can be closed again by advancing the proximal sheath portion towards the distal sheath portion by advancing slider 102.

The embodiment of FIGS. 29 to 31 is well suited to embodiments that do not include hub 150 since it avoids the need for pushing the captured filter. However, the features of the embodiment of FIGS. 29 to 31 can be used with any embodiments of the assembly described herein.

Figure 32:
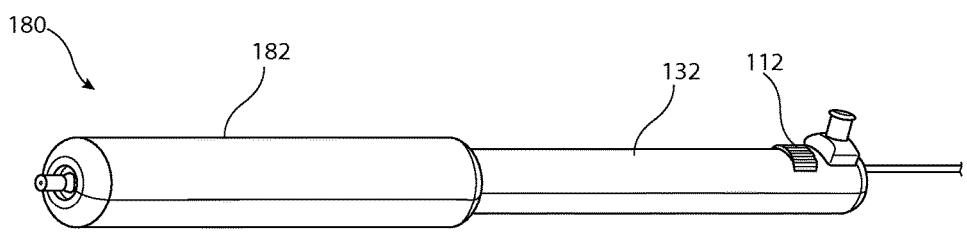
FIG. 32 is a schematic diagram in perspective view of another embodiment of a handle apparatus for a retrieval device.
Figure 33:
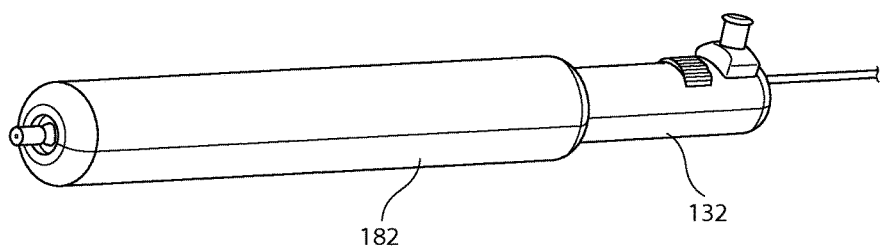
FIG. 33 is a schematic diagram in perspective view of the handle apparatus of FIG. 32 in a snaring position.
Figure 34:
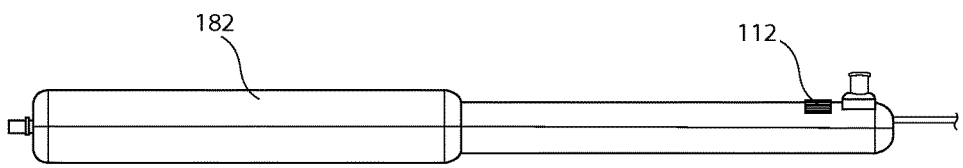
FIG. 34 is a side view of the handle apparatus of FIGS. 32 and 33.

FIGS. 32-34 show another embodiment of a deployment handle 180 for use in any of the embodiments of the assembly described herein. The deployment handle 180 includes a distal handle section 132 which corresponds in many respects to the distal handle 132 described above. However, the rotor element 112 is in this embodiment provided in a distal region of the distal handle section 132, and the slider 102 is not provided.

In this embodiment, the distal handle section 132 is coupled to the proximal sheath portion in a fixed manner. In other words, relative movement between the distal handle section 132 and the proximal sheath portion 14 is prevented.

The deployment handle 180 also includes a proximal handle section 182, which is movable with respect to the distal handle section 132. As can be seen in FIGS. 32-34, the proximal handle section 182 is coaxial with the distal handle section 132, but has a larger diameter, thereby allowing the proximal handle section 182 to slide over the distal handle section 132. However, in a modification, the proximal handle can have a smaller diameter and slide in the distal handle section.

The inner catheter 24 is held within the proximal handle section 182 in a manner corresponding to that described with respect to the handle grip 116 above so that the inner catheter 24 is not only fixed longitudinally in position within the proximal handle section 182, but it is also prevented from rotating when the carrier catheter 18 is made to rotate.

In other words, the proximal and distal sheath portions 14, 12 have a fixed relative longitudinal position with respect to, respectively, the distal and proximal handle sections 132, 182.

As shown, a flush port is provided in each end of the device to enable flushing of the different lumens found throughout the device.

In order to operate the deployment handle 180, the starting position is as shown in FIG. 32 in which the proximal handle section 182 is proximally retracted with respect to the distal handle section 132. In this position, the proximal and distal sheath portions are together in the closed position.

Once it is desired to expose the snare 22, the proximal handle section 182 is advanced in a distal direction as shown in FIG. 33. This exerts a distal force on the distal sheath portion by virtue of the inner catheter 24 which is longitudinally fixed with respect to the distal handle section 182. This causes the distal sheath portion 12 to move distally away from the proximal sheath portion 14, thereby exposing the snare.

Once the filter has been captured by the snare in the manner described above, the distal sheath portion is retracted to draw the filter into the distal sheath portion. This is achieved as shown in FIG. 34. The proximal handle section 182 is retracted in a proximal direction, which in turn draws the distal sheath portion in a proximal direction to move it into the closed position with respect to the proximal sheath portion, thereby drawing the filter into it. This leaves the sheath in the closed position with the filter inside it, and enables the filter to be withdrawn from the patient.

Embodiments of the invention can include a hub with a bail-out mechanism in place of the hub 20 described above. Examples of such bail-out mechanisms are described in connection with FIGS. 35-38. The hubs described in connection with these figures are as per the hub 20 described above except as otherwise detailed.

FIGS. 35A-C and 36A-B show a hub 190 with a distal end 192. A snare thread or wire 194 is provided similar to snare 22. However, a first end 196 of the snare is fixed to the hub 190, for example by welding 195. A second end 198 of the snare 194 is provided with a coupling element 200. In the embodiment of FIGS. 35-36, the coupling element 200 is a ball. The ball in this embodiment has a diameter of 0.75 mm, although other sizes can also be used, such as 0.7 mm. A diameter of 0.7 mm is beneficial as such balls are available as they are used in ball point pens. The ball is steel although other materials can also be used. The ball can be a part of the snare melted into a ball shape. However, the coupling element 200 does not need to be a ball; any bulge in the snare 194 can be used. In a modification, the coupling element can be in the form of a polymer (for example plastic) ring around the second end 198 of the snare 194.

The hub 190 is provided with a receiving element 202 for receiving the ball 200. In the embodiment of FIGS. 35A-C and 36A-B, the receiving element 202 is a detent in the form of a recess in the hub 190.

During normal operation of the assembly, the ball 200 is held within the recess 202 by being covered with the distal sheath portion 12. In this embodiment, the distal sheath portion 12 is configured so that during normal operation, the distal sheath portion 12 cannot be moved distally sufficiently to expose the ball 200.

The deployment handle in this embodiment is provided with a bail-out mechanism actuator 191 which is operable to provide an additional distal movement to the distal sheath portion 12 to expose the ball 200. The bail-out mechanism actuator can be provided for example in the form of a simple push button or pin which causes movement of the distal sheath portion for example by an extra 8 mm or 15 mm. Such an actuator is within the abilities of the skilled person. An example of a bail-out mechanism actuator 191 is shown in FIG. 35C in which the deployment handle corresponds to that of FIGS. 32 to 34. However, it is to be appreciated that the bail-out mechanism can be used with any of the deployment handles described herein.

The hub 190 of this embodiment provides significant advantages in terms of safety. When a medical device retrieval apparatus is manipulated in the vicinity of a filter within a patient, the snare can become snagged on the legs of the filter. This can prevent successful retrieval of the filter, and can even make retraction of the retrieval apparatus difficult.

By being able to release one end of the snare in a bail-out procedure, if the snare does become snagged on a leg of the filter, it is possible to release one end of the snare so that the snare is just a wire or thread rather than a loop. The entire medical procedure can then be aborted safely with the retrieval apparatus pulling the first end 196 of the snare, and leaving the second end 198 of the snare to unwind itself from the filter as it is drawn out of the patient.

Figure 36A:
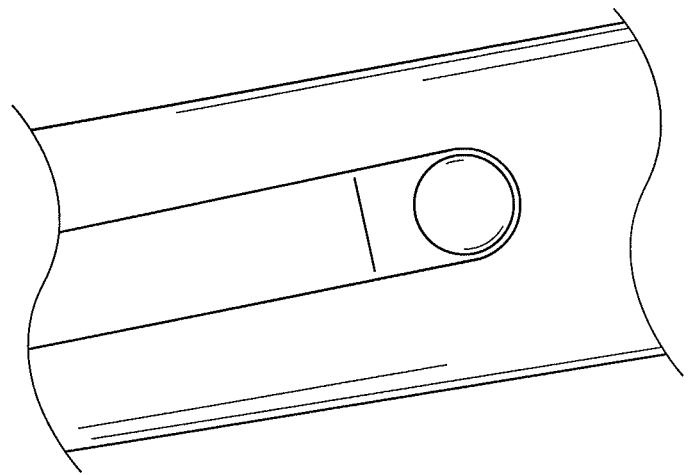
FIGS. 36A-36B are perspective views of the bail-out mechanism of FIG. 35.
Figure 36B:
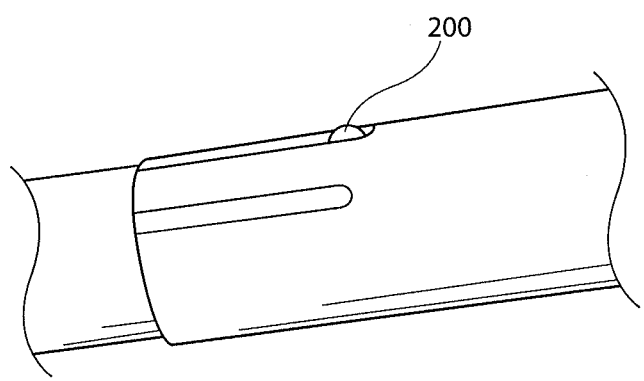

FIG. 36A shows the ball 200 in position within the recess in the hub in plan view, and FIG. 36B shows the ball 200 in place in a recess in the hub 190 in side view.

Another embodiment of a hub 206 including a bail-out mechanism in which a second end of the snare is releasable from the hub is shown in FIGS. 37A-B and 38. This embodiment corresponds in many respects to the embodiment of FIGS. 35A-C and 36A-B. However, in this embodiment, the second end 198 of the snare 194 has a coupling element in the form of a horse shoe clip 208. The hub 206 is provided with a horse shoe-shaped recess 210. The recess 210 is configured to receive and co-operate with the horse shoe clip 208.

As for the embodiment of FIGS. 35A-C and 36A-B, in normal operation, the clip 208 is covered by the distal sheath portion 12, and a bail-out mechanism actuator is provided on the deployment handle to cause extra distal movement of the distal sheath portion 12 in order to release the clip 208 to allow the snare to be removed from a filter in which it has become caught.

Although the embodiments of the snare bail-out mechanism described above discuss the coupling element as being in normal operation retained within the distal sheath portion 12, it is also possible for the coupling element in normal operation to be retained within the proximal sheath portion 14. In such a modification, corresponding changes are made to the bail-out mechanism actuator in order to move the proximal sheath portion to release the coupling element.

The embodiment of FIGS. 37A-B offers advantages in that it reduces the amount of pulling force on the snare which needs to be borne by the sheath. This can be seen from FIG. 38 which shows the forces on the hub 206 when a pulling force is being applied via the snare 194. As can be seen from FIG. 38, because of the clip shape of the coupling element in this embodiment, much of these forces are absorbed by the hub 206 itself, rather than the sheath. This is advantageous since the hub 206 is more easily made to withstand the forces applied in such a scenario. The embodiment of FIGS. 37A-B also makes creep force of the sheath unimportant.

It is preferred that the snare 22, 140, 142, 194 is made of a radiopaque material or includes radiopaque markers or material, so that the snare can be readily seen by imaging during the retrieval process. One particularly preferred material for the same is Nitinol wire covered with Tantalum for radiopacity.

It is to be understood that described herein are only some embodiments of the present invention and that the skilled person will appreciate that there is a number of modifications and alternatives to the described embodiments which fall within the scope of the claims.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A medical device retrieval apparatus comprising:
   a sheath provided with first and second sheath portions arranged coaxially when introduced together percutaneously into an incision in a patient and movable relative to one another between a snaring position and a closed position;
   a carrier catheter disposed in the sheath and movable at least relative to the first sheath portion;
   a hub attached to a distal end of the carrier catheter;
   a snare attached to the hub, the snare being locatable within the first sheath portion, the first sheath portion including a chamber in which a medical device is receivable, the snare comprising a loop structure; and
   an inner catheter disposed through the carrier catheter and fixed to the first sheath portion;
   wherein in the snaring position, a proximal end of the first sheath is positioned distal to a distal end of the second sheath portion, and the snare is locatable between the first sheath portion and a deployment handle.

2. The apparatus according to claim 1, wherein in the snaring position the first and second sheath portions are axially separated and the snare is locatable between the first and second sheath portions.

3. The apparatus according to claim 1, wherein in the closed position the first and second sheath portions abut one another or partially overlap one another.

4. The apparatus according to claim 1, including a coupling element to couple together the first and second sheath portions in the closed position.

5. The apparatus according to claim 1, wherein the loop structure is one of a loop of thread and a loop of wire.

6. The apparatus according to claim 1, wherein the snare includes a thread or wire with a first end attached to the carrier and a second end releasably attached to the carrier.

7. The apparatus according to claim 6, wherein the second end of the snare includes a coupling element and the carrier includes a receiving element to receive the coupling element.

8. The apparatus according to claim 7, wherein the coupling element is held in the receiving element by the sheath, the sheath being movable by a snare release actuator to release the coupling element from the receiving element.

9. The apparatus according to claim 7, wherein the coupling element is a bulge in the snare and the receiving element is a detent or the coupling element is a clip and the receiving element is a region of the carrier for receiving the clip.

10. The apparatus according to claim 6, including a deployment handle, the deployment handle including a snare release actuator operable to release the second end of the snare from the carrier.

11. The apparatus according to claim 1, wherein the snare is made of metal or metal alloy.

12. The apparatus according to claim 1, wherein the snare is made from platinum or palladium.

13. The apparatus according to claim 1, wherein the snare is made of shape memory material.

14. The apparatus according claim 1, wherein the snare is made from or includes radiopaque material.

15. The apparatus according to claim 1, wherein the hub is sized to be receivable in the first sheath portion.

16. The apparatus according to claim 1, wherein the assembly includes a deployment handle coupled to a proximal end of the sheath.

17. The apparatus according to claim 16, wherein the deployment handle is coupled to the second sheath portion.

18. The apparatus according to claim 16, wherein the deployment handle includes an actuator coupled to move the first and second sheath portions relative to one another.

19. The apparatus according to claim 16, wherein the deployment handle includes a carrier actuator comprising a rotation element which rotates the carrier relative to the sheath.

20. The apparatus according to claim 16, wherein the deployment handle includes a sheath actuator coupled to the first sheath portion and which pulls the first sheath portion towards the second sheath portion.

21. The apparatus according to claim 20, wherein the sheath actuator is fixed to a portion of the handle in non-rotatable manner.

22. The apparatus according to claim 20, wherein the deployment handle includes a rotatable element operable to retract the sheath actuator thereby to pull the first sheath portion towards the second sheath portion.

23. The apparatus according to claim 16, wherein the deployment handle includes a first handle section and a second handle section coupled, respectively, to the first sheath portion and the second sheath portion, wherein the first and second handle sections are movable relative to each other to move the first and second sheath portions relative to each other.

24. The apparatus according to claim 1, wherein the hub tapers in a proximal direction to define a tapered portion, the snare being attached to the hub at the tapered portion.

25. The apparatus according to claim 24, wherein the tapered portion includes at least one slit formed therethrough.

26. A method of retrieving a medical device from a patient comprising: providing the retrieval apparatus of claim 1;
- locating the sheath across a medical device to be retrieved with the first and second sheath portions extending either side of the medical device;
- moving the first and second sheath portions away from one another so as to expose the snare;
- capturing the medical device in the snare;
- pulling the medical device into the chamber of the first sheath portion; and
- closing the first and second sheath portions together with the medical device housed in the first sheath portion.

\* \* \* \* \*